United States Patent [19]

Elsheikh et al.

[11] Patent Number: 5,177,271
[45] Date of Patent: Jan. 5, 1993

[54] PRODUCTION OF VINYLIDENE FLUORIDE

[75] Inventors: Maher Y. Elsheikh, Tredyffrin; Michael S. Bolmer, Lower Providence, both of Pa.

[73] Assignee: Elf Atochem North America, Inc., Philadelphia, Pa.

[21] Appl. No.: 876,336

[22] Filed: Apr. 30, 1992

[51] Int. Cl.$^5$ .................. C07C 19/08; C07C 21/18
[52] U.S. Cl. .................................. 570/156; 570/155
[58] Field of Search ........................... 570/155, 156

[56] References Cited

U.S. PATENT DOCUMENTS 2,442,993 6/1948 Cass .
2,461,523 2/1949 Coffman et al. .
3,188,356 6/1965 Hauptschein .................. 570/155
3,456,025 7/1969 Gardner .

FOREIGN PATENT DOCUMENTS 234002 2/1987 European Pat. Off. .
54-130507 10/1979 Japan .

OTHER PUBLICATIONS

Satterfield, Heter. Catal. in Practice, 206-208 (1980).
Hudlicky Chem. of Org Fluor Compds., 218 (1976).
Walker et al., J. Org Chem., 30, 3284 (1965).

Primary Examiner—A. Alan Siegel

[57] ABSTRACT

Production of vinylidene fluoride by contacting 143a and HCl in the gas phase at 300–700 C.

4 Claims, No Drawings

PRODUCTION OF VINYLIDENE FLUORIDE

FIELD OF THE INVENTION

This invention is directed to the production of vinylidene fluoride ("VDF") from 1,1,1-trifluoroethane ("143a") and hydrogen chloride ("HCl"), more particularly to a gas phase process for the copyrolysis of 143a and HCl.

BACKGROUND OF THE INVENTION

VDF is a useful monomer in the preparation of fluorocarbon polymers which have excellent weathering and chemical resistance properties. A copending application filed on even date herewith, attorney docket number IR 3245, describes a process for the gas phase catalytic hydrofluorination of vinylidene chloride ("VDC") to yield a product stream rich in 1-chloro-1,1-difluoroethane ("142b"), 1,1-dichloro-1-fluoroethane ("141b"), HCl, and 143a, and the subsequent conversion of the resulting 142b and HCl to VDF. Since 143a is a by-product of the catalytic hydrofluorination step, it would be desirable to also have a viable process for directly converting impure 143a/HCl product mixtures into VDF.

Several processes have been reported for converting pure 143a (specifically or generically) into VDF monomer [U.S. Pat. Nos. 2,461,523; 2,442,993; and 3,456,025; F. H. Walker et al., J. Org. Chem., 30, p. 3284 (1965); and Japanese Patent Application 54-130507].

The presence of HCl in the process of this invention makes the result unpredictable. For example, it is known that HCl can be readily oxidized with air to form chlorine gas [C. N. Satterfield, Heterogeneous Catalysis in Practice, McGraw Hill (1980) 206-208] and, subsequently, that the chlorine generated can be used to chlorinate the methyl group of 143a [M. Hudlicky, Chemistry of Organic Fluorine Compounds, Ellis Horwood Limited (1976) 218] to form 1,1,1-trifluoro-2-chloroethane, which in turn can be dehydrofluorinated into 1,1-difluoro-2-chloroethylene. These products can not be readily converted back into 143a or VDF.

SUMMARY OF THE INVENTION

A process for producing VDF is provided wherein 143a and HCl are reacted in the vapor phase at a temperature of from about 300 to about 700 degrees Centigrade ("C"), with or without a catalyst. Suitable catalysts include (a) an oxygen-containing gas such as air or oxygen, (b) a metal salt such as aluminum fluoride, or (c) a metal salt and a gas containing oxygen, carbon dioxide, or both.

The process can be utilized in either batch or, preferably, continuous fashion, as described in more detail hereinafter.

DETAILED DESCRIPTION OF THE INVENTION

It has now been unexpectedly found that 143a/HCl mixtures, such as those resulting from the gas phase catalytic hydrofluorination of VDC, can be pyrolyzed in the vapor phase to give good yields of VDF monomer. While batch or continuous processes may be used, the process will be described in detail hereinbelow primarily in terms of the preferred continuous operation.

In the continuous process the 143a/HCl mixture and gas catalyst, if any, are continuously fed in the vapor phase to a reactor (typically tubular in design) which may optionally be filled with a supported or unsupported metal salt catalyst and generally maintained at a temperature of from about 300° C. to about 700° C., preferably at about 400°-600° C. Generally, the HCl and 143a are contacted at a molar ratio of from about 1:1 to about 10:1, preferably from about 2:1 to about 4:1. Typically the reactants are in contact for from about 5 about 200 seconds, preferably from about 10 to about 120 seconds. The reaction is generally carried out at atmospheric pressure.

When an oxygen-containing gas such as air or oxygen is used as a catalyst for the process, it is generally employed in an amount having an oxygen content of from about 1 to about 10 mole %, based on the total feed of 143a, HCl, and oxygen, preferably about 1.5-7.0%.

When a metal salt is used as a catalyst, it is generally selected from aluminum fluoride (such as in the form of fluorided gamma-aluminum oxide) or a salt of a transition metal element such as chromium, cobalt, nickel, or iron. The salt, such as a chloride, nitrate, or oxide, will be converted into the corresponding fluoride upon activation with hydrogen fluoride. The supported catalysts may be employed, for example, in the form of pellets or granules. It is advantageous to cofeed with the metal salt a gas containing oxygen, carbon dioxide, or both. If air or oxygen is used as the gas, it is generally employed in the amounts set forth above. When a carbon dioxide containing gas is used, the carbon dioxide content can vary from about 20 to about 75 mole %, based on the total feed of 143a, HCl, and carbon dioxide, preferably 30-50%.

The materials of construction for the pyrolysis reactor are not critical, except that they should possess the necessary structural and physical characteristics to withstand the reaction conditions.

By employing the optimal conditions the process can be made selective for VDF, which can be recovered from the reactor by known techniques. For example, HCl and HF by-products may be removed by passing the products from the reactor through a scrubbing tower countercurrent to an alkaline stream made up, for example, of an aqueous hydroxide such as potassium, sodium, or calcium hydroxide, typically a 20% KOH solution. The scrubbed product may then be passed to a drying tower, packed with a suitable drying agent such as anhydrous calcium sulfate, to remove water, and the organics separated by high pressure distillation. The co-products, primarily comprised of 1-chloro-1-fluoroethylene ("VClF") and 1,1-dichloroethylene ("VDC"), can be recycled to the fluorination reaction and fluorinated into 143a.

The present invention is illustrated in more detail below by reference to the following non-limiting examples. In these examples the pyrolysis product stream was scrubbed and dried, then analyzed with a gas chromatograph ("G.C."). Optimum conditions are not necessarily used in the examples, which are intended primarily to show the effects of various catalysts and conditions on conversion and selectivity for VDF.

EXAMPLE 1

Aluminum Fluoride ($AlF_3$) As A Catalyst In The Presence of Oxygen or Carbon Dioxide 36 Grams of gamma-alumina were loaded into a pyrolysis reactor and activated at 650° C. with air (20 ccm), followed by HF activation at 550° C., using about 10 ccm of nitrogen. Various mixtures of 143a, HCl, and air or carbon dioxide were then fed to the reactor at the temperatures and contact times noted in Table I below, shown in Table I, together with the G.C. product analysis.

TABLE I

| Temp. | Time (sec) | % CO2 | % O2 | % Conv. | % VDF | % VDC | % VClF |
|---|---|---|---|---|---|---|---|
| Example 1 | | | | | | | |
| 503 | 14 | 50 | 0 | 48.6 | 62.3 | 7.2 | 19.9 |
| 550 | 12 | 44.6 | 0 | 44.7 | 77.8 | 0.4 | 15.7 |
| 550 | 17 | 0 | 5.9 | 91.1 | 32.9 | 24.8 | 25.8 |
| Example 2 | | | | | | | |
| 548 | 88 | 0 | 2.8 | 22.8 | 70.9 | 0.4 | 15.6 |
| 551 | 62 | 0 | 1.9 | 42.3 | 70.5 | 0.4 | 21.4 |
| Example 3 | | | | | | | |
| 500 | 71 | 0 | 0 | 7.7 | 71.5 | <2.0 | 13.9 | together with the amount of carbon dioxide or air (oxygen content) and the G.C. analysis for the major resulting products (in mole %). The mole % of HCl and 143a in the feed in the three runs were 30.1:19.9, 36.6:18.8, and 63.8:30.3, respectively.

EXAMPLE 2

Oxygen As Catalyst

Mixtures of 143a (49.3% and 33.4%, respectively), HCl (47.9% and 64.7%, respectively), and air (oxygen content shown in Table I below) were fed to the reactor at the temperatures and contact times noted in Table I, together with the G.C. analysis of major resulting products.

EXAMPLE 3

Absence of Catalyst

A mixture of 30.1% 143a and 69.9% HCl was fed to an empty reactor at the temperature and contact time

What is claimed is:

1. A process for producing vinylidene fluoride which comprises the steps of (a) heating in the vapor phase a mixture comprising 1,1,1-trifluoroethane and hydrogen chloride at a temperature of from about 300° C. to about 700° C., and (b) recovering vinylidene fluoride.

2. A process as in claim 1 wherein step (a) is conducted in the presence of an oxygen-containing gas, a metal salt, or a metal salt and a co-fed gas containing oxygen, carbon dioxide, or both.

3. A process as in claim 1 wherein the molar ratio of hydrogen chloride to 1,1,1-trifluoroethane is from about 2:1 to about 4:1.

4. The process of claim 1 wherein the 1,1,1-trifluoroethane and hydrogen chloride feed is the product mixture resulting from the gas phase catalytic hydrofluorination of vinylidene chloride.

* * * * *